United States Patent [19]
Westcott et al.

[11] Patent Number: 5,728,115
[45] Date of Patent: Mar. 17, 1998

[54] PERFUSION CLAMP

[75] Inventors: Roy A. Westcott; Richard Putz, both of Indianapolis, Ind.

[73] Assignee: Indiana University Foundation, Bloomington, Ind.

[21] Appl. No.: 581,190

[22] Filed: Dec. 29, 1995

[51] Int. Cl.$^6$ .................................................. A61B 17/00
[52] U.S. Cl. ........................... 606/151; 606/157; 604/250
[58] Field of Search ................................. 606/158, 157, 606/151, 150; 604/250; 24/474, 476, 495, 505, 517, 525, 573.5, 581, 588

[56] References Cited

U.S. PATENT DOCUMENTS

| | | | |
|---|---|---|---|
| 2,215,122 | 9/1940 | Hess | 24/517 |
| 4,800,879 | 1/1989 | Gloyakhovsky et al. | 606/157 |
| 4,821,719 | 4/1989 | Fogarty | 606/158 |
| 5,571,125 | 11/1996 | Chadwick | 606/158 |

FOREIGN PATENT DOCUMENTS

| 4100219 | 7/1992 | Germany | 606/158 |
|---|---|---|---|

*Primary Examiner*—Jeffrey A. Schmidt
*Attorney, Agent, or Firm*—Woodard, Emhardt, Naughton Moriarty & McNett

[57] ABSTRACT

A renal perfusion clamp which is capable of opening to 180 degrees. The perfusion clamp of the present invention additionally allows for interchange of variously sized clamp heads in order to accommodate aortic cuffs of various sizes. The perfusion clamp provides for adjustable clamping force which is controllable by the perfusionist.

27 Claims, 3 Drawing Sheets

5,728,115

PERFUSION CLAMP

TECHNICAL FIELD OF THE INVENTION

The present application relates generally to surgical clamping devices and, more particularly, to a perfusion clamp.

BACKGROUND OF THE INVENTION

During the transplantation of a donor kidney from one patient to another, the kidney is kept at a lowered temperature during the period of time between harvesting the kidney from the donor patient until the kidney is transplanted into the receiving patient. During this period of time in which the kidney is not connected to the body's blood supply, it has been found useful to pump a solution of perfusate into the renal aorta to ensure that semi-normal kidney function occurs immediately after the transplant operation has been completed.

In order to couple the perfusion cannula to the renal aorta, a prior art clamping device has been developed. This prior art device is illustrated in FIGS. 1-3 and indicated generally at 10. The clamp 10 is manufactured by Pilling Company of Fort Washington, Pa. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an integral clamp head 24, while the distal end of the member 14 includes an integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in clamping relationship unless an external compressive force is applied to the handles 18 and 20.

Referring to FIG. 2, it can be seen in this view that the distal end of the member 12 comprises an elongated, hollow, annular clamp head 24. The upper surface 30 of clamp head 26 is visible through the hollow center of annular clamp head 24. Also visible in FIG. 2 is a lumen 32 which extends through the nipple 28.

The clamp 10 is illustrated in use in FIG. 3. The clamp 10 is attached to the renal aorta 34 of a donor kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34.

The prior art clamp 10 exhibits several problems which increase the difficulty in using the clamp 10 during perfusion of donor kidneys. First, the smallest available size of the clamp 10 has an annular clamp head 24 of 10 mm×15 mm. This requires a tissue size at the distal end 38 of the renal aorta 34 of at least 15 mm×20 mm in order to seal the clamp 10 for efficient perfusion. This amount of aortic tissue is not always available. Second, the clamp 10 will not open more than 30°. This creates considerable difficulty for the surgeon in placing the aortic tissue in place prior to clamping. Third, the spring 22 that applies pressure to the clamp tends to be ineffective and does not properly seal the aortic tissue in order to prevent leakage of perfusion fluid. Fourth, the overall length of the clamp 10 creates a problem of fitting the clamp 10 inside the perfusion cassette. If multiple arterial cannulations are required, the area constraints pose even greater problems.

Given the problems with the prior art renal perfusion clamp 10, the perfusionist has two alternate methods of cannulation to his/her discretion. One is to insert a plastic cannula into the artery and suture it into place. This process causes the arterial tissue from the suture back to the aortic cuff to necrose, which significantly shortens the artery length usable during the transplant operation. The other alternative is to suture more aortic tissue (if available) around the distal end 38 of the artery 34 in order to create a sufficient amount of tissue to effectively use the clamp 10. This procedure significantly increase the amount of time that the organ 36 must remain on ice, which detrimentally effects the preservation of the organ.

There is therefore a need for a perfusion clamp which overcomes the problems inherent in the prior art design. The present invention is directed toward meeting this need.

SUMMARY OF THE INVENTION

The present invention relates to a renal perfusion clamp which is capable of opening to 180 degrees. The perfusion clamp of the present invention additionally allows for interchange of variously sized clamp heads in order to accommodate aortic cuffs of various sizes. The perfusion clamp provides for adjustable clamping force which is controllable by the perfusionist.

In one form of the invention a perfusion clamp is disclosed, comprising: (a) a first longitudinal arm; (b) a second longitudinal arm; (c) a cross-member, wherein a first end of the cross-member is coupled to a proximal end of the first arm and a second end of the cross-member is coupled to a proximal end of the second arm, wherein at least one of the first and second ends pivots at its coupling; (d) a first clamp head coupled to a distal end of the first arm; (e) a second clamp head coupled to a distal end of the second arm; (f) an adjustable clamping member coupled to one of the first and second arms and operative to releasably maintain the first and second clamp heads in clamping engagement with adjustable force.

In another form of the invention a perfusion clamp is disclosed, comprising: (a) a first longitudinal arm; (b) a second longitudinal arm; (c) a pivotal coupling between the first and second arms; (d) a first clamp head releasably coupled to a distal end of the first arm; and (e) a second clamp head coupled to a distal end of the second arm; wherein the first and second clamp head may be brought into clamping engagement by pivoting the first and second arms about the pivotal coupling; and wherein the first clamp head may be uncoupled from the first arm for replacement by a third clamp head of a different size.

In another form of the invention, a kit is disclosed, comprising: (a) a plurality of first clamp heads, each of said plurality of first clamp heads having a different head size; and (b) a perfusion clamp, comprising: (i) a first longitudinal arm, adapted to releasably engage any one of the plurality of first clamp heads at a distal end of the first arm; (ii) a second longitudinal arm; (iii) a pivotal coupling between the first and second arms; and (iv) a second clamp head coupled to a distal end of the second arm; wherein one of the plurality of first clamp heads is engaged with the first arm; and wherein the one first clamp head and the second clamp head may be brought into clamping engagement by pivoting the first and second arms about the pivotal coupling.

DETAILED DESCRIPTION OF THE PREFERRED EMBODIMENT

Figure 1:
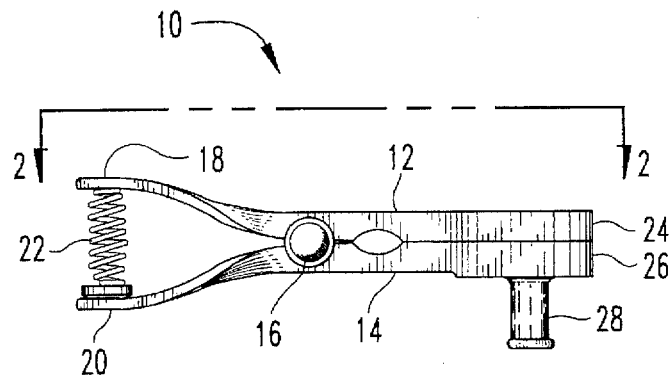
FIG. 1 is a side elevational view of a prior art perfusion clamp.
Figure 2:
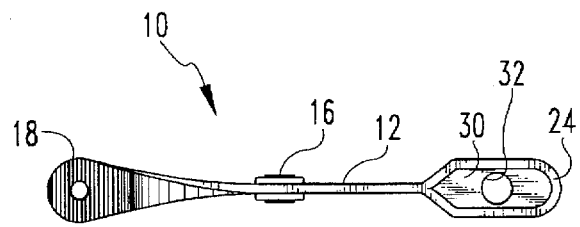
FIG. 2 is a top plan view of the prior art perfusion clamp of FIG. 1.
Figure 3:
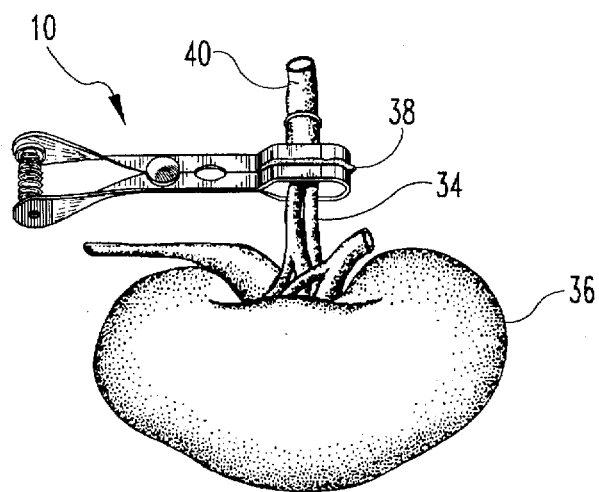
FIG. 3 is a perspective view of the prior art perfusion clamp of FIG. 1 in use with a donor kidney.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In order to overcome the problems inherent in the prior art devices, the renal perfusion clamp of the present invention incorporates a novel hinge design that allows the clamp to be opened to 180 degrees. Such a wide opening angle gives greater flexibility to the perfusionist when installing the clamp to the renal aortic cuff. In order to further facilitate such installation, the clamp of the present invention incorporates a detachable clamp head which may be interchanged with clamp heads of various sizes in order to more particularly match the clamp to the aortic cuff. Finally, the clamp of the present invention provides for an adjustable clamping force, thereby giving greater clamping control to the perfusionist.

Figure 4:
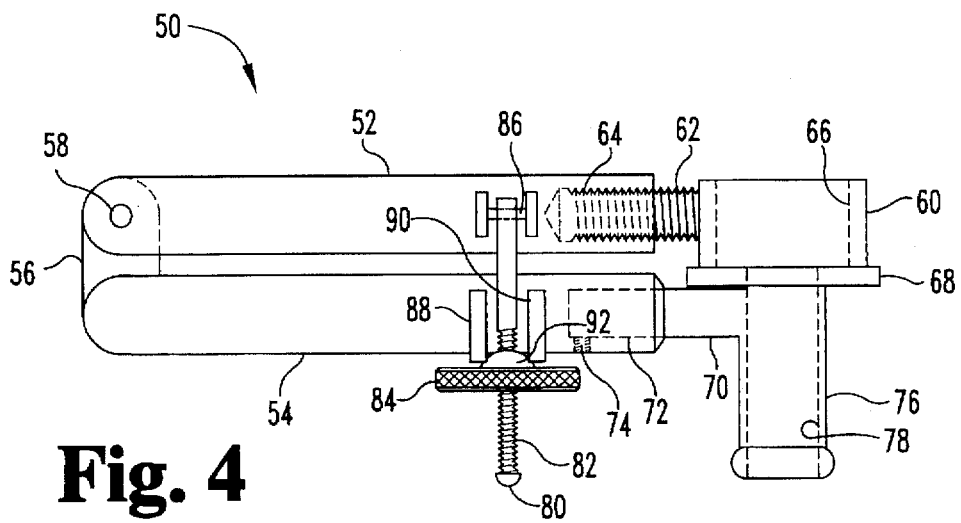
FIG. 4 is a side elevational view of a preferred embodiment perfusion clamp of the present invention in a closed position.

Referring to FIG. 4, there is illustrated a side elevational view of the preferred embodiment perfusion clamp of the present invention, indicated generally at 50. The clamp 50 comprises a first longitudinal member 52 and a second longitudinal member 54 joined by an intermediate member 56. The intermediate member 56 is fixedly attached to the longitudinal member 54 and pivotally attached to the longitudinal member 52 by means of a pin 58. The ability of the longitudinal member 52 to pivot about the pin 58 allows the clamp 50 to be opened to greater than 180°, thereby allowing unobstructed access to the distal end 38 of the renal aorta 34 during placement of the clamp 50.

A first clamp head 60 is releasably mounted to an end of the longitudinal member 52 such as by means of an integral threaded member 62 which engages the threaded bore 64 in the longitudinal member 52. The clamp head 60 includes a central bore 66 therethrough. A second clamp head 68 is releasably coupled to the longitudinal member 54 such as by means of engagement of the attachment member 70 with the bore 72 in the longitudinal member 54. The member 70 is fixed within the bore 72 by means of a set screw 74. The clamp head 68 includes an attached nipple 76. An open perfusion lumen 78 extends through the nipple 76 and the clamp head 68.

Figure 5:
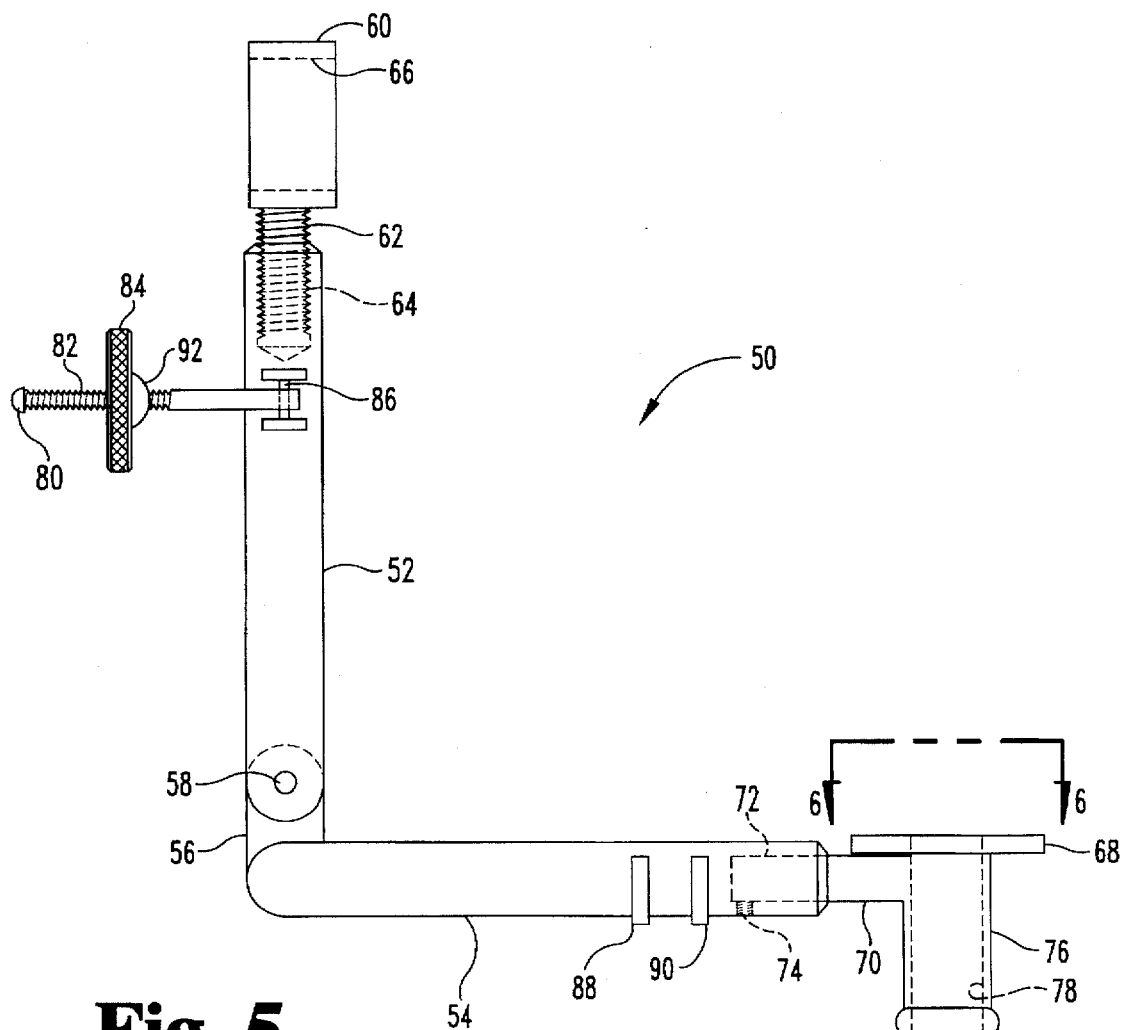
FIG. 5 is a side elevational view of the preferred embodiment perfusion clamp of the present invention in an open position.

When the longitudinal members 52 and 54 of the clamp 50 are brought together, the clamp head 60 engages the clamp head 68 in order to clamp the distal end 38 of a renal aorta 34 which has been inserted through the bore 66 and folded over the clamp head 60. The clamp 50 is maintained in the clamping position by means of a clamping bar 80. The clamping bar 80 has a threaded portion 82 upon which is engaged a threaded thumb wheel 84, such that rotation of the thumb wheel 84 causes linear translation of the position of the thumb wheel 84 upon the clamping bar 80. The clamping bar 80 is pivotally mounted to the longitudinal member 52 by means of a pin 86 which extends through the clamping bar 80. The pin 86 is fixed to the longitudinal member 52. When the clamping bar 80 is laid across the longitudinal member 52 as shown in FIG. 4, it lies between the posts 88 and 90 which are attached to the exterior surface of the longitudinal member 54. The thumb wheel 84 is then rotated until the hemispherical portion 92 of the thumb wheel 84 engages the underside of the members 88 and 90. Once the thumb wheel 84 is tightened in this manner, the clamping bar 80 is prevented from pivoting on the pin 86 by interaction between the hemispherical member 92 and the members 88 and 90. Strong and positive clamping force is thereby provided between the clamp head 60 and 68 of the perfusion clamp 50. The clamp 50 may easily be released by rotating the thumb wheel 84 in the opposite direction until the hemispherical member 92 is clear of the members 88 and 90, at which point the clamping bar 80 may be pivoted on the pin 86 in order to release the clamp. The clamp 50 is illustrated in its open position in FIG. 5.

Figure 6:
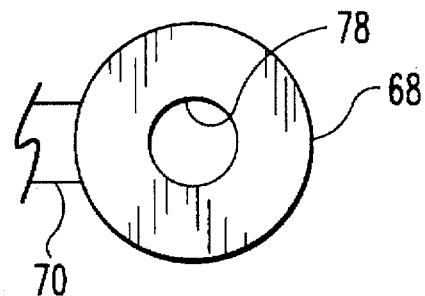
FIG. 6 is top plan view of a second clamp head of the present invention.
Figure 7A:
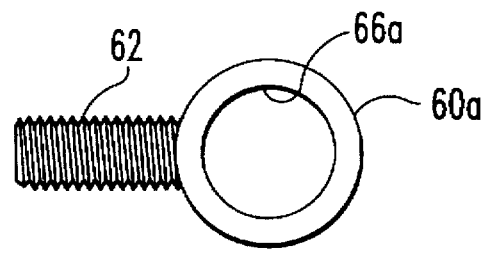
FIG. 7A–C are top plan views of various sizes of a first clamp head of the present invention.
Figure 7B:
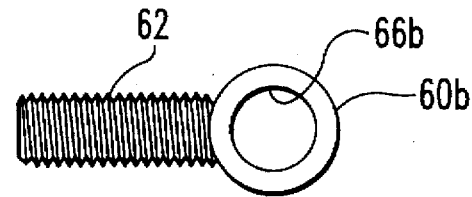
Figure 7C:
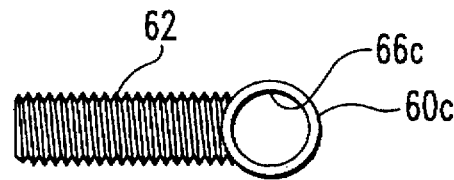

Referring to FIG. 6, a top plan view of the clamp head 68 is illustrated. The perfusion lumen 78 extends through the clamp head 68 as well as the nipple 76. The wide annular surface area 80 of the clamp head 68 allows use of variously sized clamp heads 60. Because the clamp head 60 is threadingly engaged with the longitudinal member 52, it is possible to interchange various sizes of the clamp head 60 in order to particularly suit the clamp 50 to the size of the artery being clamped. Replacement of the clamp head 60 is simply a matter of opening the clamp 50, unscrewing the clamp head 60, and screwing in a new clamp head 60 having the appropriate sized head. As illustrated in FIGS. 7A–C, clamp heads 60A–C may be manufactured having various diameters and various sizes of bores 66A–66C. By including an assortment of such clamp heads, the clamp 50 is configurable to meet different sized aortic cuff requirements. The ability to adapt the clamp 50 in the field according to the amount of aortic cuff around the artery is a very desirable feature of the present invention. Furthermore, the ability of the clamp 50 to be opened to 180° for ease of arterial tissue insertion makes the clamp 50 much easier to use than the prior art clamp 10. Furthermore, the adjustable clamping bar 80 and threaded thumb screw 82 provide positive clamping force between the clamp heads 60 and 68 which is adjustable, thereby giving complete clamping control to the perfusionist. It will therefore be appreciated by those skilled in the art that the clamp 50 of the present invention represents a substantial improvement over the prior art clamp 10.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the perfusion clamp of the present invention may be used in conjunction with perfusion of any body organ, and is not restricted to renal perfusion.

What is claimed is:

1. A perfusion clamp, comprising
 (a) a first longitudinal arm;
 (b) a second longitudinal arm;
 (c) A cross-member, wherein a first end of the cross-member is coupled to a proximal end of the first arm and a second end of the cross-member is coupled to a proximal end of the second arm, wherein at least one of the first and second ends pivots at its coupling;
 (d) a first clamp head coupled to a distal end of the first arm;
 (e) a second clamp head coupled to a distal end of the second arm, said second clamp head including an integral nipple and a perfusion lumen extending therethrough; and
 (f) an adjustable clamping member coupled to one of the first and second arms and operative to releasably maintain the first and second clamp heads in clamping engagement with adjustable force.

2. The perfusion clamp of claim 1, wherein the first clamp head is releasably coupled to the first arm.

3. The perfusion clamp of claim 2, wherein the first clamp head includes an integral threaded member, the first arm includes a longitudinal threaded bore at its distal end, and the threaded member and the threaded bore are threadingly engaged.

4. The perfusion clamp of claim 1, wherein the first clamp head includes a transverse bore therethrough.

5. The perfusion clamp of claim 1, wherein the second clamp head is releasably coupled to the second arm.

6. The perfusion clamp of claim 5, wherein the second clamp head includes an integral attachment member, the second arm includes a longitudinal bore at its distal end, and the attachment member and the longitudinal bore are releasably engaged.

7. The perfusion clamp of claim 6, wherein the second arm includes a set screw extending transversely through the second arm and into the longitudinal bore, wherein engagement of the set screw with the attachment member prevents disengagement of the attachment member from the longitudinal bore.

8. A perfusion clamp, comprising:
 (a) a first longitudinal arm;
 (b) a second longitudinal arm;
 (c) A cross-member, wherein a first end of the cross-member is coupled to a proximal end of the first arm and a second end of the cross-member is coupled to a proximal end of the second arm, wherein at least one of the first and second ends pivots at its coupling;
 (d) a first clamp head coupled to a distal end of the first arm;
 (e) a second clamp head coupled to a distal end of the second arm;
 (f) an adjustable clamping member coupled to one of the first and second arms and operative to releasably maintain the first and second clamp heads in clamping engagement with adjustable force; said clamping member comprising:

(i) a clamping bar having a first end pivotally coupled to the first arm and a threaded second end; and
  (ii) a thumbwheel threadingly engaged with the threaded second end; wherein the first and second clamp heads may be maintained in clamping engagement by engagement of the thumbwheel with the second arm.

9. The perfusion clamp of claim 8, wherein the thumbwheel includes a hemispherical portion and the second arm includes at least one post thereon, wherein interaction between the hemispherical portion and the at least one post maintains the first and second clamp heads in clamping engagement.

10. A perfusion clamp, comprising;
 (a) a first longitudinal arm;
 (b) a second longitudinal arm;
 (c) a pivotal coupling between the first and second arms;
 (d) a first clamp head releasably coupled to a distal end of the first arm; and
 (e) a second clamp head coupled to a distal end of the second arm, the second clamp head including an integral nipple and a perfusion lumen extending therethrough; wherein the first and second clamp head may be brought into clamping engagement by pivoting the first and second arms about the pivotal coupling; and wherein the first clamp head may be uncoupled from the first arm for replacement by a third clamp head of a different size.

11. The perfusion clamp of claim 10, further comprising:
 a clamping member coupled to one of the first and second arms and operative to releasably maintain the first and second clamp heads in clamping engagement.

12. The perfusion clamp of claim 11, wherein the clamping member comprises:
 (a) a clamping bar having a first end pivotally coupled to the first arm and a threaded second end; and
 (b) a thumbwheel threadingly engaged with the threaded second end;
 wherein the first and second clamp heads may be maintained in clamping engagement by engagement of the thumbwheel with the second arm.

13. The perfusion clamp of claim 12, wherein the thumbwheel includes a hemispherical portion and the second arm includes at least one post thereon, wherein interaction between the hemispherical portion and the at least one post maintains the first and second clamp heads in clamping engagement.

14. The perfusion clamp of claim 10, wherein the first clamp head includes an integral threaded member, the first arm includes a longitudinal threaded bore at its distal end, and the threaded member and the threaded bore are threadingly engaged.

15. The perfusion clamp of claim 10, wherein the first clamp head includes a transverse bore therethrough.

16. The perfusion clamp of claim 10, wherein the second clamp head is releasably coupled to the second arm.

17. The perfusion clamp of claim 16, wherein the second clamp head includes an integral attachment member, the second arm includes a longitudinal bore at its distal end, and the attachment member and the longitudinal bore are releasably engaged.

18. The perfusion clamp of claim 17, wherein the second arm includes a set screw extending transversely through the second arm and into the longitudinal bore, wherein engagement of the set screw with the attachment member prevents disengagement of the attachment member from the longitudinal bore.

19. A perfusion clamp, comprising
(a) a first longitudinal arm having a proximal end and a distal end, said first arm including a first clamp head at the distal end;
(b) a second longitudinal arm having a proximal end and a distal end, said second arm including a second clamp head at the distal end, the second clamp head including a nipple and a perfusion lumen extending therethrough;
(c) a pivotal coupling between said first and second longitudinal arms on the proximal ends thereof; and
(d) an adjustable clamping member coupled to one of the first and second arms and operative to releasably maintain the first and second clamp heads in clamping engagement with adjustable force.

20. The perfusion clamp of claim 19, wherein the first clamp head is releasably coupled to the first arm.

21. The perfusion clamp of claim 20, wherein the first clamp head includes an integral threaded member, the first arm includes a longitudinal threaded bore at its distal end, and the threaded member and the threaded bore are threadingly engaged.

22. The perfusion clamp of claim 19, wherein the first clamp head includes a transverse bore therethrough.

23. The perfusion clamp of claim 19, wherein the second clamp head is releasably coupled to the second arm.

24. The perfusion clamp of claim 23, wherein the second clamp head includes an integral attachment member, the second arm includes a longitudinal bore at its distal end, and the attachment member and the longitudinal bore are releasably engaged.

25. The perfusion clamp of claim 24, wherein the second arm includes a set screw extending transversely through the second arm and into the longitudinal bore, wherein engagement of the set screw with the attachment member prevents disengagement of the attachment member from the longitudinal bore.

26. The perfusion clamp of claim 19, wherein the clamping member comprises:
(a) a clamping bar having a first end pivotally coupled to the first arm and a threaded second end; and
(b) a thumbwheel threadingly engaged with the threaded second end; wherein the first and second clamp heads may be maintained in clamping engagement by engagement of the thumbwheel with the second arm.

27. The perfusion clamp of claim 26, wherein the thumbwheel includes a hemispherical portion and the second arm includes at least one post thereon, wherein interaction between the hemispherical portion and the at least one post maintains the first and second clamp heads in clamping engagement.

* * * * *